Figure 1:
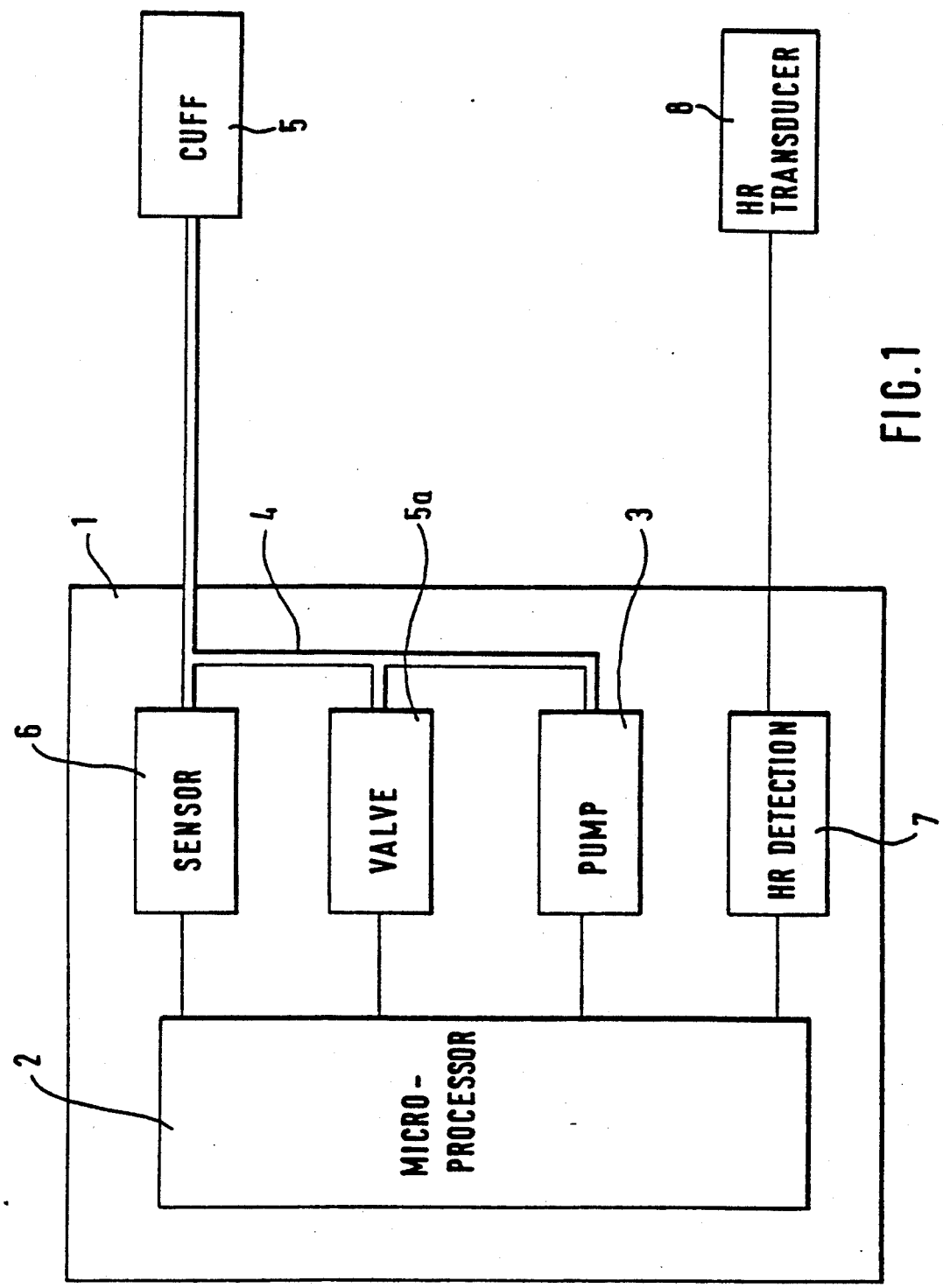

United States Patent

Zapf et al.

Patent Number: 5,215,096
Date of Patent: Jun. 1, 1993

[54] METHOD AND APPARATUS FOR AUTOMATIC BLOOD PRESSURE MONITORING

[75] Inventors: Christian Zapf, Herrenberg; Michael Frankenreiter, Sindelfingen, both of Fed. Rep. of Germany

[73] Assignee: Hewlett Packard Company, Palo Alto, Calif.

[21] Appl. No.: 725,182

[22] Filed: Jul. 3, 1991

[30] Foreign Application Priority Data

Oct. 26, 1990 [EP] European Pat. Off. ......... 90120518.7

[51] Int. Cl.⁵ .............................................. A61B 5/022
[52] U.S. Cl. ................................... 128/682; 128/680
[58] Field of Search ......................... 128/672, 677–686

[56] References Cited

U.S. PATENT DOCUMENTS

| | | | |
|---|---|---|---|
| 4,312,359 | 1/1982 | Olson | 128/680 |
| 4,349,034 | 9/1982 | Ramsey, III | 128/681 |
| 5,103,830 | 4/1992 | Shinomiya | 128/672 |

FOREIGN PATENT DOCUMENTS

| | | |
|---|---|---|
| 0079305A3 | 10/1982 | European Pat. Off. . |
| 0123313A3 | 4/1984 | European Pat. Off. . |
| A20208520 | 4/1986 | European Pat. Off. . |
| 0208520A2 | 7/1986 | European Pat. Off. . |
| A10353315 | 1/1988 | European Pat. Off. . |
| A10353316 | 1/1988 | European Pat. Off. . |
| 0353315A1 | 8/1988 | European Pat. Off. . |
| 0353316A1 | 8/1988 | European Pat. Off. . |
| 90120518 | 6/1991 | European Pat. Off. . |
| 3703458A1 | 2/1987 | Fed. Rep. of Germany . |

Primary Examiner—William E. Kamm
Assistant Examiner—Kevin Pontius
Attorney, Agent, or Firm—Perman & Green

[57] ABSTRACT

A non-invasive automatic blood pressure monitor uses the oscillometric technique. That is, a cuff is inflated and then deflated in discrete deflation steps, while the oscillations caused by movement of the arterial walls are recorded during each deflation step. If no oscillations occur, the deflation step is interrupted when a predetermined time period ($t_{max}$) has expired. According to the invention, said predetermined time period ($t_{max}$) is varied according to the heart rate (step 13). This leads to considerable reduction of required time for each measurement.

22 Claims, 4 Drawing Sheets

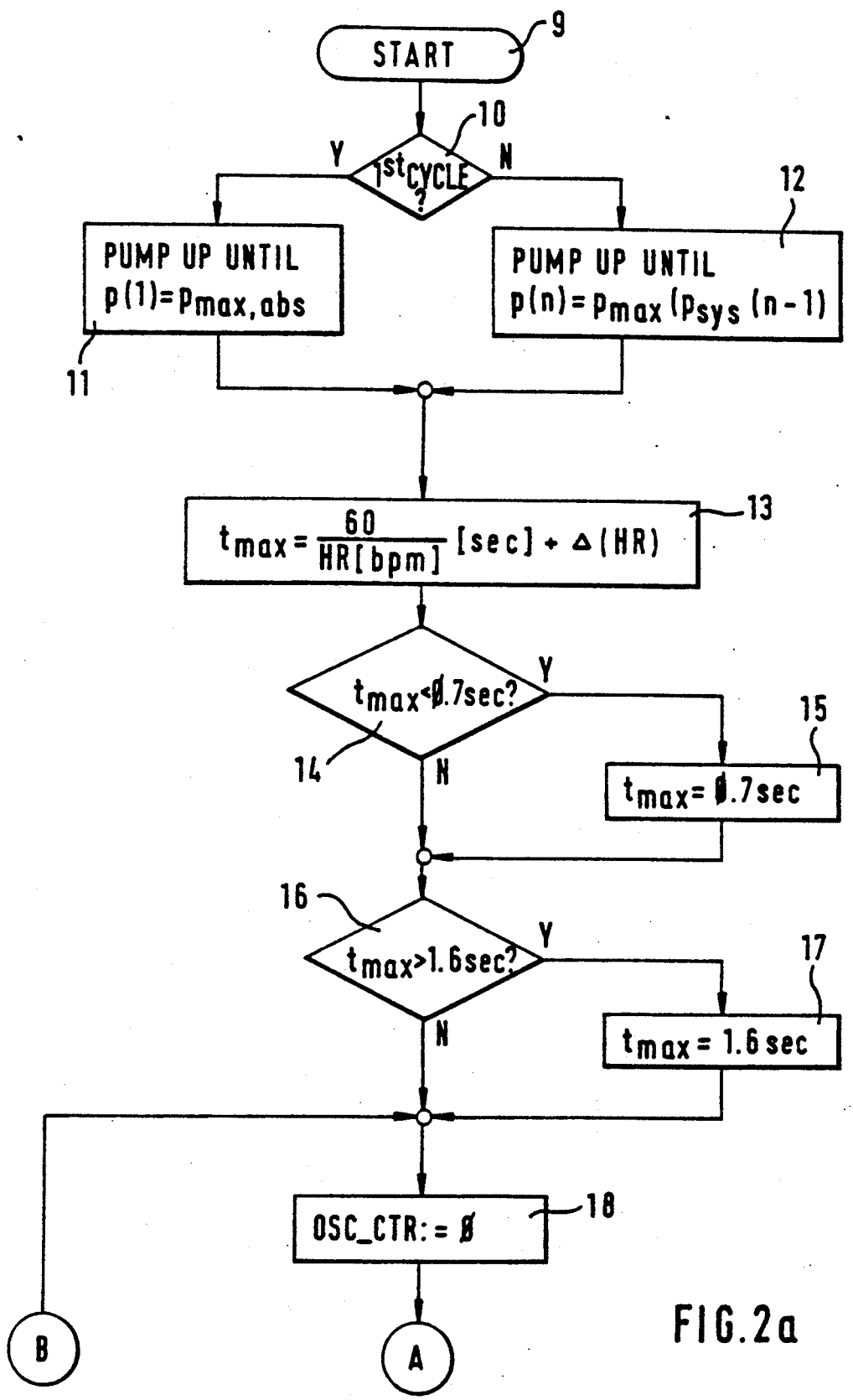

METHOD AND APPARATUS FOR AUTOMATIC BLOOD PRESSURE MONITORING

The present invention relates to a method for automatic non-invasive monitoring of a patient's blood pressure, comprising the steps of:
- applying a cuff around a limb of the patient,
- inflating said cuff to a predetermined pressure,
- stepwise reducing the pressure applied to said cuff,
- holding the applied pressure constant at each step until
  - at least one superimposed oscillation caused by a heartbeat has occurred, or until
  - a predetermined time period has expired,
- measuring the amplitudes of said superimposed oscillations and processing them in order to determine either the systolic, the diastolic or the mean blood pressure, or a combination of them.

The invention also relates to an apparatus able to perform the inventive method.

The manual method of measuring a patient's blood pressure in non-invasive manner comprises the application of a pressure cuff to a limb, e.g. an arm, of the patient. The cuff is then pumped up to a pressure above the systolic blood pressure of the patient. The arteries in the limb of the patient are thereby occluded. The cuff pressure is now continuously decreased while the physician or the nurse monitor the occurrence of the sounds indicative of the start and the end of the opening of the arteries (Korotkoff sounds). The pressure readings at the points in time when said sounds occur represent the systolic and the diastolic blood pressure.

There have been attempts to perform the above measurement, also called auscultation technique, on an automatic basis, i.e. by means of a monitor able to pump up a blood pressure cuff on a periodic basis and to record the Korotkoff sounds via a microphone during deflation. However, the reading of these monitors was not always reliable.

The most commonly used technique for automatic blood pressure monitoring is nowadays the so-called oscillometric method which uses the oscillations or fluctuations of the walls of the arteries which occur in synchronism with the blood pulse. According to the oscillometric technique, the cuff is pumped up to a pressure beyond the systolic pressure of the patient and is then deflated in discrete steps. During each step (where the cuff pressure is held constant), a pressure sensor records the oscillations caused by movement of the arterial walls and superimposed on the constant cuff pressure. The amplitudes of these oscillations, preferably the peak-to-peak amplitudes, are recorded. As soon as a certain amount of oscillations have been observed during a certain pressure step, the cuff pressure is reduced by a certain amount, so that oscillations may be recorded during the next step.

The amplitudes of the observed oscillations, or the envelope of their peak values, are then used to determine either the systolic, the diastolic or the mean blood pressure. For the details of this measurement technique, and the evaluation of the oscillations, reference is e.g. made to the following publications: U.S. Pat. No. 4,349,034, EP-A-208520, EP-A-353315 and EP-A-353316.

In the design process of an automatic blood pressure monitor, it has to be taken into account that, although the measurement as such is based on a non-invasive technique, the appliance of counterpressure and the temporary occlusion of arteries imposes stress on the patient. In particular, the recurring appliance of counterpressure which is necessary to obtain a quasi-continuous blood pressure recording causes embarrassing sensations. Such sensations may lead to defensive movement of the patient, which in turn causes, by means of sudden pressure changes, artifacts. The artifacts either disturb or at least prolong the measurement cycle. Such may happen in particular if the patient suffers from a trauma, as well as in the case of post-operative patients or neonates.

It is therefore a primary design goal of automatic non-invasive blood pressure monitoring devices to keep the measurement cycles (i.e. the time period between the application of counter-pressure and complete deflation of the cuff) as short as possible. One approach to shorten the measurement cycle is e.g. to adapt the height of the deflation steps, i.e. the pressure difference between two steps, to the patient in order to minimize the number of necessary steps. This method is described in the above-mentioned European patent application EP-A-353315.

It is a major objective of the present invention to provide a method and an apparatus which allows further reduction of the duration of a blood pressure measurement.

According to the above described method, this object is solved by the steps of
- determining the time interval between the heart beats, or the heart rate, of a patient, and
- calculating and/or varying the predetermined time period in dependence of the time interval, or in dependence of the inverse of the heart rate, such that the duration of the predetermined time period is increased when said time interval increases, or when said heart rate decreases.

The new approach of the present invention is that it takes the duration of a single pressure step in the deflation process into account. The duration of such step may be determined by two factors:

a) As soon as a predetermined number of oscillations have been observed at a certain pressure level (usually two oscillations), the pressure may be decreased to the next step. This time cannot be shortened.

b) On the other hand, it may also happen that no oscillations or oscillations of an amplitude too small to indicate a heart beat are observed at a certain pressure level. This is particularly true at the beginning of the measurement—when the cuff pressure still exceeds the systolic blood pressure of the patient—, or at the end of the measurement—when the cuff pressure is below the patient's diastolic blood pressure. There are possibilities to avoid the second case, e.g. by performing the necessary calculations as measurement goes on and to deflate the cuff completely as soon as the diastolic blood pressure has been detected, but there is no way to avoid the phase between application of the maximum cuff pressure and the onset of the first oscillations. This is particularly true at the first measurement cycle; as the patient's systolic blood pressure is not known at that point in time, there may be a significant difference between the initially applied cuff pressure and the beginning of the first oscillations. In subsequent measurements, the initial cuff pressure may be adapted to the systolic blood pressure detected during the preceding measurement cycle; however the initial pressure has still to be significantly higher than the systolic blood pressure—otherwise, an increase in the systolic blood pressure of the patient could not be recorded.

In prior art blood pressure monitors, a maximum length or duration of a single pressure step has been specified. If no oscillations were observed during said maximum length or duration, the cuff pressure was reduced to the next level. However, as oscillations can only be observed during a heart beat, and as the monitor should also be operative in cases of patients with a low heart rate, the maximum duration of a single step was considerable. For example, in case of a patient with a heart rate of 40 bpm (beats per minute), the maximum duration had been set to 1.5 secs (or, under safety aspects, even above that), as this duration corresponds to the time interval between two consecutive heart beats. If several pressure steps were necessary before the first oscillations could be observed, the total time required to wait for oscillations (which did not occur) could even exceed the time required for taking the actual measurement.

The present invention makes use of the fact that several state-of-the-art monitors are multi-channel monitors able to record several patient parameters of diagnostic importance. One standard parameter is for example the electro-cardiogram (ECG). If not only the blood pressure, but also the ECG is recorded, a peak trigger may detect the QRS complexes in the ECG so that either the time interval between consecutive heart beats, or, in turn, the heart rate may be calculated. Once either of these parameters is known, it is now possible to adapt the maximum duration (or "predetermined time period") at a single pressure level to the known heart rate of the patient. That is, once the time interval between heart beats, or the heart rate, of a patient is known, the waiting time for an oscillation can be reduced. If no oscillation occurs, the pressure may be reduced at an earlier point in time, dependent on the heart rate or the time interval between consecutive heart beats. The time required to perform a complete measurement is thereby considerably reduced, around 25% on an average. For the first measurement—when the systolic blood pressure of the patient is still unknown—the reduction may even be 50%.

The primary contribution of the present invention is therefore that the overall time required to take a measurement is considerably reduced by adaptation of the maximum time period at each pressure level to the heart rate of the patient. It is understood that there are several choices for the determination of the time interval between the heart beats, or the heart rate. The electrocardiogram has already been discussed above. Instead, a plethysmogram recording, in particular an optical plethysmogram, may be used to detect the blood pulse and, therefore, the heart rate. The same information can also be obtained from an optical oxygen saturation transducer, as e.g. described in German Offenlegungsschrift DE-OS 37 03 458. In an invasive blood pressure sensor is applied, its blood pulse signals could also be used to determine the heart rate. Last not least - particularly if no further parameter than non-invasive blood pressure is available (e.g. in the case of a stand-alone monitor with non-invasive blood pressure only)—it is also possible to use the oscillations appearing in the blood pressure recording as an indication of the heartbeat and to measure their distance in time, e.g. from one oscillation maximum to the next one. This also gives an indication of the time interval between heartbeats, resp. the heart rate. It is understood that there are further possibilities to determine the heart rate of a patient parameter if this parameter is indicative of the blood pulse or the heart activity of the patient.

It is also evident that the monitor need not necessarily be a multi-parameter monitoring device. Instead, it is sufficient that a signal indicative of the heart activity is measured, in addition to the non-invasive blood pressure. Likewise, an externally generated (e.g. by a second monitor) signal indicative of the heart beats or the heart rate could be fed to a monitor which is only equipped to measure the blood pressure noninvasively.

It is possible to determine the heart rate, or the time interval between heart beats, from beat to beat. However, it is preferred to have an averaged value as this ensures that single artefacts, an extrasystole or the like do not considerably influence the calculated maximum duration of the time period at a certain pressure level. An averaged heart rate may e.g. be obtained by taking the time interval between n consecutive heart beats, dividing it by n and then taking the inverse of it.

It is also a matter of choice at which points in time the duration of the time period at a certain pressure level is adapted to the heart activity of the patient. Although it is preferred to calculate the time period prior to each measurement and to keep it constant during this measurement, it is also possible to make a new calculation prior to each deflation step, or in turn, to keep said time period constant for a complete set of measurements.

Further, the invention comprises calculation of the time period, as well as other methods of varying the duration of it. For example, a look-up table may be provided—as will be described below—, which makes it unnecessary to spend processor time for calculation.

In a preferred embodiment of the invention, the predetermined time period is substantially proportional to the time interval between heartbeats, or inversely proportional to the heart rate. That is, the duration of the time period is calculated by means of the following equation $$t_{max} = \Delta t \quad (1)$$

wherein $t_{max}$ is the maximum time period at a certain deflation step and $\Delta t$ is the time interval between the heart beats (as mentioned above, this can also be an averaged value). Likewise, $t_{max}$ can be calculated according to the following equation:

$$t_{max} \frac{60}{HR[bpm]} \ [sec] \quad (2)$$

wherein HR is the heart rate in beats per minute (and may also be calculated on an average basis).

Alternatively, the maximum time period may also be calculated or determined by a discrete function, by a non-linear function or the like. It is even possible to assign certain ranges to the predetermined time period, e.g. to select $t_{max} = 1$ sec for any heart rate between 50 and 70 bpm.

According to another preferred embodiment, an offset is added to the predetermined time period. This is done for safety reasons, in order not to miss a heart beat if the heart rate goes down. Said offset may either be a constant, or a variable which depends on the heart rate. In the latter case, the offset is preferably increased when the heart rate goes up. As an example, the offset may be 0.2 sec for a heart rate beyond 120 bpm and 0.3 sec for a heart rate smaller or equal to 120 bpm.

According to an advantageous solution, the predetermined time period is limited or "clamped" to an upper and/or lower limit. That is, if the calculated or otherwise determined time period falls below a lower limit, it is set to this lower limit. In similar manner, it can be avoided that the time period exceeds an upper limit. The lower limit is mainly provided for safety reasons, whereas the upper limit is provided in order to avoid excessive time periods which do not relate to a physiologically meaningful heart rate.

As already mentioned, the predetermined time period may also be determined by a look-up table. This is particularly useful if a microprocessor is used to control operation of the blood pressure monitor. A look-up table contains a cross-reference between the heart rate and the predetermined time period, or between the heart beat time interval and the predetermined time period. The look-up table may be built such that it already comprises a constant or variable offset and/or upper and lower limits, so that no further calculations have to be made once a time period value has been revealed from the table. The look-up table may also be arranged in ranges, e.g. assign a time period value of $t_{max} = 1$ sec to any heart rate between 80 and 90 bpm (this already includes the above mentioned offset).

The invention also relates to an apparatus for non-invasive measuring of a patient's blood pressure comprising
- cuff inflation means, in particular a pump,
- cuff deflation means, in particular a valve,
- at least a pressure sensor,
  - wherein said cuff inflation means, said cuff deflation means and said pressure sensor are set up for pneumatic connection with a cuff for appliance around the patient's limb,
- control means operatively connected with said cuff inflation means, said cuff deflation means and said pressure sensor, said control means being set up to inflate the cuff to a predetermined pressure and to stepwise reduce the applied pressure, said control means further being set up to hold the applied pressure constant at each step until at least one superimposed oscillation has been observed or until a predetermined time period has expired,
- blood pressure calculation means, particularly a microprocessor, for calculating the systolic, the diastolic and/or the mean blood pressure from the amplitudes of the superimposed oscillations recorded by said pressure sensor.

Said apparatus is characterized by
- heart rate determination means or interval measuring means for measuring the time interval between the heart beats, and
- time period calculation means set up to calculate said predetermined time period in dependence of the heart rate indicated by said heart rate determination means or in dependence of the time interval between the heart beats indicated by said interval measuring means.

As already mentioned, said apparatus may be a blood pressure-only monitor, in which case an external signal indicative of the heart rate or of the interval between heart beats has to be provided, or a monitor able to determine and process not only the non-invasive blood pressure, but also another parameter indicative of the patient's heart activity. In a preferred embodiment, said time period calculation means comprises a look-up table which holds values or ranges of the heart rate and of the corresponding values of the predetermined time period.

Further features and advantages of the invention can be found in the claims as well as in the detailed description.

Figure 2B:
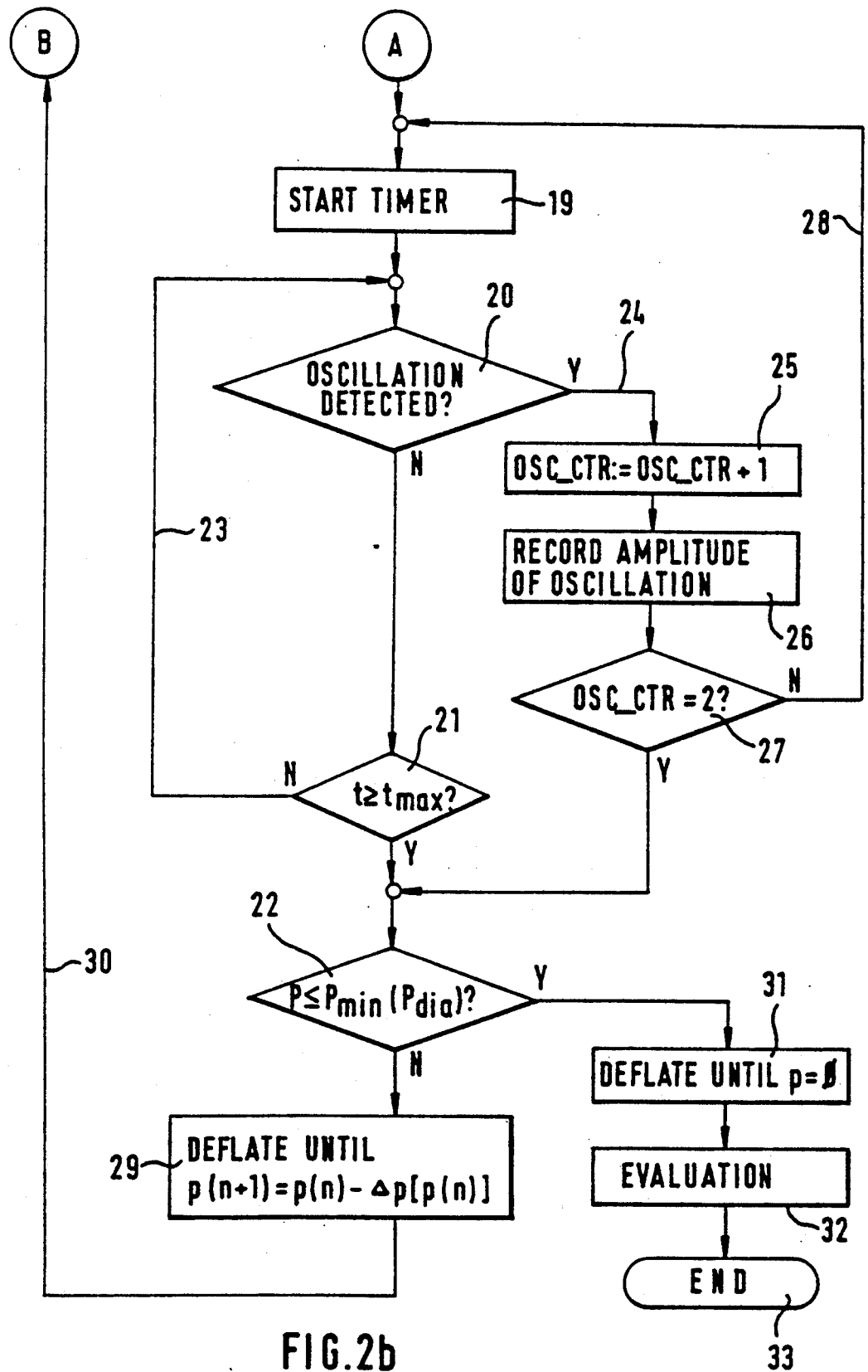
Figure 3:
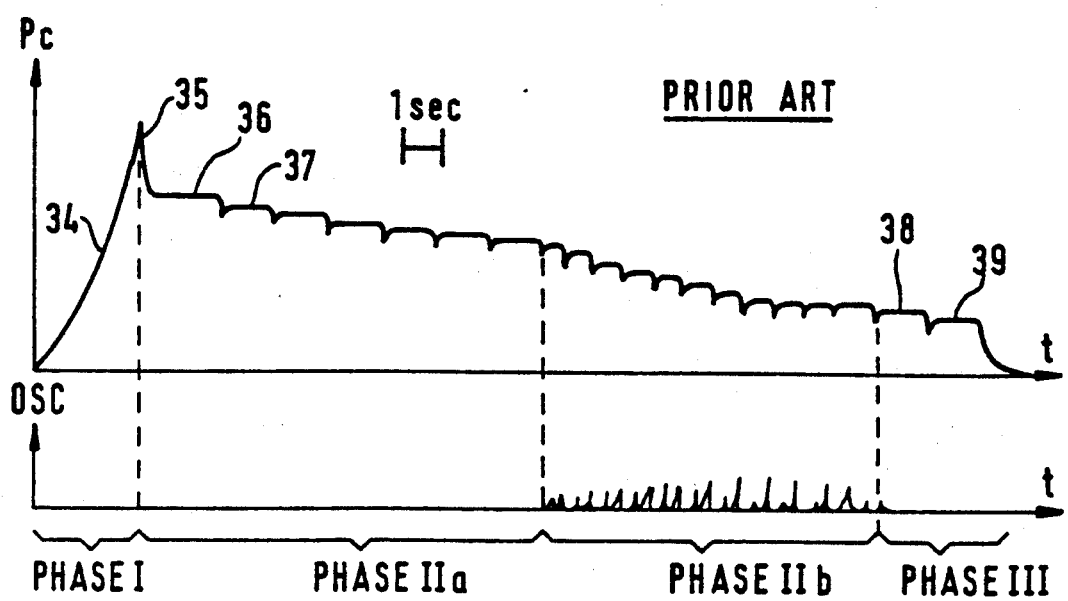
Figure 4:
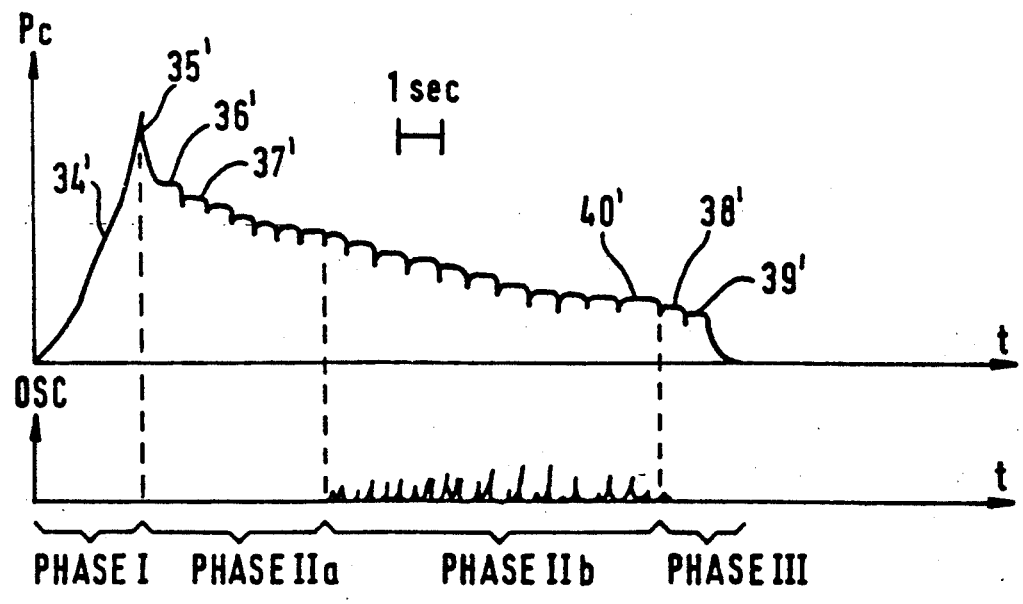

The invention will now be explained, by means of a non-limiting example, with reference to the accompanying drawings, in which:

FIG. 1 depicts a schematic block diagram of the major components of a blood pressure monitor according to the invention, FIGS. 2a and 2b depict, by means of a flow chart, the basic steps of operation, as far as the invention is concerned, FIG. 3 depicts a pressure diagram of a single measurement, as well as a timing diagram of the superimposed oscillations, of a prior art blood pressure monitor and FIG. 4 depicts timing diagrams of the cuff pressure and of the oscillations of a blood pressure monitor according to the invention.

The basic components of a blood pressure monitor according to the invention are shown in FIG. 1. Monitor 1 comprises a microprocessor 2 for controlling monitor operation and calculating the blood pressure. The microprocessor is operatively connected with a pressure pump 3 which in turn, is connected via pneumatic tubes or hoses 4 with a cuff 5 for application around a patient's arm.

A releasable connection in the pneumatic system, necessary to disconnect the cuff from the monitor, is not shown in FIG. 1.

Microprocessor 3 further controls a valve 5a and a pressure sensor 6, which are also connected with the pneumatic system.

A heart rate detection circuit 7 is electrically connected with a heart rate transducer 8 and with microprocessor 2. Heart rate transducer 8 may e.g. consist of ECG (electrocardiogram) electrodes, in which case heart rate detection circuit 7 comprises a peak trigger circuit for detection of the QRS complexes. (If the oscillations in the blood pressure recording are used to determine the heart rate, elements 7 and 8 may be omitted). The calculation of the heart rate may either be performed by heart rate detection circuit 7 or —preferably—by microprocessor 2.

In operation, valve 5a is initially closed. Microprocessor 2 causes pump 3 to increase the pressure in cuff 5 to a predetermined maximum. The cuff pressure is then reduced stepwise in that valve 5 is opened for short time periods. At each of these steps ("deflation steps"), pressure sensor 6 records the oscillations superimposed on the cuff pressure, which relate to the movement of the arterial walls during a blood pulse. Microprocessor 2 uses the peak-to-peak amplitudes of the oscillations to determine the systolic, the diastolic and/or the mean blood pressure of the patient. After a certain delay—usually, between 5 and 15 minutes —, the next measurement is started. In contrast thereto, the heart rate is recorded continuously.

FIGS. 2a and 2b depict the basic flow chart of microprocessor operation. It relates to a single measurement, i.e. it is entered at label "START" (reference number 9) each time a measurement (determination of blood pressure) is started.

After start of the measurement, the processor first determines whether this is the first measurement of a measurement cycle, i.e. at a certain patient (reference number 10). If yes, the cuff is pumped up to an absolute maximum pressure, reference number 11, as the expected systolic blood pressure of the patient is still unknown. However, differences may be made in the absolute maximum pressure $p_{max}$ between adults and neonates.

If it is not the first cycle, i.e. the patient's systolic blood pressure of the previous cycle is known, the cuff pressure is increased to a pressure which depends on the systolic blood pressure of the last cycle (reference number 12).

In the next step 13, the predetermined time period $t_{max}$ is calculated according to the equation given there. HR means the heart rate in beats per minute and $\Delta$ means the safety offset, which itself depends on the heart rate. That is, the safety offset is longer for low heart rates and shorter for high heart rates.

The calculated predetermined time period $t_{max}$ is then compared with a lower limit, which is 0.7 sec in this case (reference number 14). If it is lower than said limit, the predetermined time period is set to the lower limit of 0.7 sec, see step 15. Otherwise, it remains unchanged.

In similar manner, $t_{max}$ is compared with an upper limit of 1.6 sec (reference number 16) and set to this upper limit if it was exceeded (reference number 17).

In step 18 a variable OSC_CTR is set to zero. This variable is used to count the oscillations observed at a single deflation step. Operation then proceeds, via label "A", to box 19 (FIG. 2b) where a timer is started. This timer counts the duration of each single deflation step.

The monitor then waits for an oscillation to occur at the present deflation step (reference number 20). If no oscillation has been detected, the system checks whether the predetermined time period $t_{max}$ has been exceeded (reference number 21), i.e. whether an oscillation can still be expected or whether the heart rate of the patient indicates that the possible time between two heart beats has already been exceeded, so that no further oscillation can be expected at the present deflation step. If the predetermined time period $t_{max}$ has been exceeded, operation proceeds to step 22 which will be explained later. Otherwise, the system continues to search for the next oscillation (path 23).

If an oscillation has been detected (path 24), the variable OSC_CTR ("oscillation counter") is increased by one, see step 25. Then, the peak-to-peak amplitude of the oscillation is recorded for further processing (step 26). In step 27, it is checked whether variable OSC_CTR has already reached its final value of 2, i.e. the monitor described by means FIGS. 2a and 2b waits for two oscillations at each deflation step. (It is understood that this is a matter of choice, i.e. the monitor could also be designed to wait for one oscillation, or for more than two oscillations, at each deflation step). If the variable OSC_CTR has not reached its final value of 2, this means that, at a present deflation step, only one oscillation has occurred, and the process is started again (path 28).

If two oscillations have been recorded, or if the predetermined time period $t_{max}$ has been exceeded, operation proceeds to step 22. At this point, the monitor checks whether the cuff pressure p is below a minimum pressure $p_{min}$, which itself depends on the patient's diastolic pressure $p_{dia}$ of the previous cycle. If no previous cycle exists—i.e. if it is the first measurement—, an absolute value of the minimum pressure is used instead.

In case the minimum cuff pressure has not yet been reached, operation proceeds to step 29. In this step, the cuff pressure is reduced by one step, i.e. the cuff pressure $p(n+1)$ of the next cycle equals the cuff pressure $p(n)$ of the present cycle minus a pressure difference $\Delta p$. Preferably, the value of $\Delta p$ (the "step height") is also dependent on the present cuff pressure $p(n)$, as e.g. described in European patent application EP-A-353 315. The monitor then starts with the measurement at the next deflation step (step 30).

It was determined in step 22 that the cuff pressure is below the minimum pressure, the cuff is completely deflated (step 31). The recorded oscillations are then evaluated (step 32) in order to determine the systolic, the diastolic and/or the mean blood pressure of the patient. In step 33, operation stops.

The whole procedure, starting with label 9, is initiated repeatedly in the course of monitoring a patient. For example, measurements may be taken every 10 or 15 minutes.

The flowchart in FIGS. 2a and 2b shows only the steps directly relating to the present invention. It is understood that other parts of monitor operation, e.g. the determination of the height of the deflation steps, or the evaluation of the peak-to-peak amplitudes of the oscillations, are processed in more detail as shown in FIGS. 2a and 2b.

The major advantage of the invention, i.e. to make the measurement cycles shorter, is illustrated by means of FIGS. 3 and 4. FIG. 3 depicts a diagram of the cuff pressure $p_c$ over time (upper diagram), together with the observed oscillations OSC (lower diagram), of a prior art monitor.

As can be seen in the upper diagram of FIG. 3, the cuff pressure is first increased to a certain maximum pressure which is beyond the patient's systolic blood pressure (reference number 34). This is also called "PHASE I" of a measurement cycle.

After an overshoot 35, the cuff pressure $p_c$ stabilizes at the pressure level of the first deflation step 36. At this pressure level, no oscillation can be observed as the cuff pressure is still significantly beyond the patient's systolic blood pressure. In the example of FIG. 3, the monitor is specified for a heart rate of at least 40 bpm. This means that the pressure level at deflation step 36 has to be kept for at least 1.5 secs, as it may still happen that an oscillation occurs. For safety reasons, a maximum waiting time of 1.6 secs, as drawn in FIG. 3, is necessary.

The same applies to the next deflation step 37, and to all subsequent deflation steps in PHASE IIa (where no oscillations can be observed).

During PHASE IIb, oscillations occur. That is, the pressure at a certain deflation step has only to be kept until two (or more, or less) oscillations have been recorded.

In PHASE III, no further oscillations occur. Therefore, the cuff pressure $p_c$ has to be constant for further 1.6 seconds at deflation step 38, as well as at deflation step 39. After deflation step 39, it may be decided that no further oscillations can be expected, so that the cuff can completely be deflated.

It is evident that the prior art monitor loses a considerable amount of time in waiting for oscillations that will never occur. This is particularly illustrated by the fact that PHASE IIa—although meaningless for the result of the measurement—is even longer than PHASE IIb, where the actual measurement is done.

In contrast thereto, FIG. 4 depicts the corresponding diagrams for a blood pressure monitor according to the invention. In this example, it is assumed that the monitor has detected a patient's heart rate of 120 bpm. Therefore, the average time interval between heart beats is 0.5 sec. For safety reasons, the predetermined time period $t_{max}$ is set to 0.7 sec.

In FIG. 4, identical reference numbers (with additional apostrophe) have been used for the same parts of the curves, as in FIG. 3.

There is no difference between the prior art monitor and the monitor according to the invention during PHASE I. However, a significant difference occurs during PHASE IIa, as the length of the deflation steps is now 0.7 sec instead of 1.6 sec. Each of the deflation steps 36', 37' and the subsequent deflation steps during PHASE IIa are therefore considerably shorter than the corresponding deflation steps 36, 37 etc. in FIG. 3.

PHASE IIb in FIG. 4 is identical to PHASE IIb in FIG. 3. It will be noted that deflation step 40' is longer in time than any of the deflation steps during PHASE IIa. This is simply because two oscillations are recorded; therefore, the maximum duration of a single deflation step during PHASE IIb is $2 \times t_{max}$.

Deflation steps 38' and 39' (PHASE III) are again considerably shorter than the corresponding steps 38 and 39 in FIG. 3.

A comparison of the diagrams in FIGS. 3 and 4 reveals that a blood pressure monitor according to the invention is primarily superior to the prior art monitor because of the reduction of time required to process PHASE IIa. It has to be conceded that the difference in the duration of a single measurement between the new monitor and the prior art monitor is smaller if the patient has a heart rate smaller than 120 bpm. Further, the superiority of the new monitor depends on the amount of steps during PHASE IIa, i.e. on the amount of steps which are necessary until the first oscillations occur. However, on an average basis, 25% of the total measuring time can be saved. In absolute values, the saving is around 5 secs if we assume 5 deflation steps during PHASE IIa.

Further, the saving is more significant during the first measurement cycle—as the patient's systolic blood pressure is not known at that point in time—than during the subsequent cycles.

In the drawings of FIGS. 3 and 4, the oscillations have been drawn in separate diagrams, although they are superimposed to the cuff pressure. This has simply been done for graphical reasons, as their amplitude is so small that they would hardly be observable in the diagrams of the cuff pressure. The scale of the diagrams showing the oscillations is therefore different from the scale of the cuff pressure $p_c$.

We claim:

1. Method for automatic non-invasive monitoring of a patient's blood pressure, comprising the steps of:
   applying a cuff (5) around a limb of the patient;
   inflating said cuff (5) to a predetermined pressure;
   step-wise reducing the pressure applied to said cuff (5);
   holding the applied pressure constant at each step until at least one superimposed oscillation caused by a heartbeat has occurred, or until a predetermined time period ($t_{max}$) has expired, whichever occurs first;
   measuring amplitudes of said superimposed oscillations and processing them in order to determine at least one of the following: systolic, diastolic, mean blood pressure, characterized by the steps of:
   determining a time interval between heart beats, of the patient; and
   varying said predetermined time period ($t_{max}$) in dependence on said determined time interval, such that the duration of said predetermined time period ($t_{max}$) is increased when said time interval increases.

2. Method according to claim 1, characterized in that said predetermined time period ($t_{max}$) is substantially proportional to said time interval.

3. Method according to claim 2, characterized by adding an offset ($\Delta$) to said predetermined time period ($t_{max}$), said offset ($\Delta$) being a constant.

4. Method according to claim 2, characterized by adding an offset ($\Delta$) to said predetermined time period ($t_{max}$), said offset ($\Delta$) being a variable which depends on said time interval.

5. Method according to claim 1, characterized in that said predetermined time period ($t_{max}$) is compared with limits, and is set equal to a limit when $t_{max}$ falls outside of a range between said limits.

6. Method according to claim 1, characterized in that said predetermined time period ($t_{max}$) is determined from a look-up table.

7. Apparatus for non-invasive measuring of a patient's blood pressure comprising:
   cuff inflation means,
   cuff deflation means,
   a pressure sensor (6),
   wherein said cuff inflation means, said cuff deflation means and said pressure sensor (6) are set up for pneumatic connection with a cuff (5) for application around a patient's limb,
   control means operatively connected with said cuff inflation means, said cuff deflation means and said pressure sensor (6), said control means being set up to inflate the cuff (5) to a predetermined pressure and to step-wise reduce the applied pressure, said control means further being set up to hold the applied pressure constant at each step until at least one superimposed oscillation has been observed or until a predetermined time period ($t_{max}$) has expired, whichever occurs first,
   blood pressure calculation means, including a microprocessor (2), for calculating the systolic, the diastolic or the mean blood pressure from the amplitudes of the superimposed oscillations recorded by said pressure sensor (6), characterized by:
   interval measuring means for measuring the time interval between heart beats, and
   time period calculation means set up to calculate said predetermined time period ($t_{max}$) in dependence on the time interval between the heart beats indicated by said interval measuring means.

8. Apparatus according to claim 7, characterized in that said time period calculation means comprises a look-up table which holds values of said predetermined time period.

9. Apparatus according to claim 7, characterized in that said interval measuring means comprises electrocardiogram recording means and peak trigger means, said electrocardiogram recording means being set up for connection with electrocardiogram electrodes.

10. Apparatus according to claim 7, characterized in that said interval measuring means comprises plethysmogram recording means and peak trigger means, said plethysmogram recording means being set up for connection with a plethysmogram transducer or an oxygen saturation transducer.

11. Apparatus according to claim 7, characterized in that said interval measuring means comprises blood pressure recording means and peak trigger means.

12. Method for automatic non-invasive monitoring of a patient's blood pressure, comprising the steps of:
applying a cuff (5) around a limb of the patient;
inflating said cuff (5) to a predetermined pressure;
step-wise reducing the pressure applied to said cuff (5);
holding the applied pressure constant at each step until at least one superimposed oscillation caused by a heartbeat has occurred, or until a predetermined time period ($t_{max}$) has expired, whichever occurs first;
measuring amplitudes of said superimposed oscillations and processing them in order to determine at least one of the following: systolic, diastolic, mean blood pressure, characterized by the steps of:
determining the heart rate of the patient; and
varying said predetermined time period ($t_{max}$) in dependence on the inverse of said heart rate, such that the duration of said predetermined time period ($t_{max}$) is increased when said heart rate decreases.

13. Method according to claim 12, characterized in that said predetermined time period ($t_{max}$) is substantially inversely proportional to said heart rate.

14. Method according to claim 13, characterized by adding an offset ($\Delta$) to said predetermined time period ($t_{max}$), said offset ($\Delta$) being a constant.

15. Method according to claim 13, characterized by adding an offset ($\Delta$) to said predetermined time period ($t_{max}$), said offset ($\Delta$) being a variable which depends on said heart rate.

16. Method according to claim 12, characterized in that said predetermined time period ($t_{max}$) is compared with limits, and is set equal to a limit when ($t_{max}$) falls outside of a range between said limits.

17. Method according to claim 12, characterized in that said predetermined time period ($t_{max}$) is determined via a look-up table.

18. Apparatus for non-invasive measuring of a patient's blood pressure comprising:
cuff inflation means,
cuff deflation means,
a pressure sensor (6),
wherein said cuff inflation means, said cuff deflating means and said pressure sensor (6) are set up for pneumatic connection with a cuff (5) for application around a patient's limb,
control means operatively connected with said cuff inflation means, said cuff deflation means and said pressure sensor (6), said control means being set up to inflate the cuff (5) to a predetermined pressure and to step-wise reduce the applied pressure, said control means further being set up to hold the applied pressure constant at each step until at least one superimposed oscillation has been observed or until a predetermined time period ($t_{max}$) has expired, whichever occurs first,
blood pressure calculation means, including a microprocessor (2), for calculating the systolic, diastolic or mean blood pressure from the amplitudes of the superimposed oscillations recorded by said pressure sensor (6) characterized by:
heart rate determination means (7),
time period calculation means set up to calculate said predetermined time period ($t_{max}$) in dependence on the heart rate indicated by said heart rate determination means (7).

19. Apparatus according to claim 18, characterized in that said time period calculation means comprises a look-up table which holds heart rate values and corresponding values of said predetermined time period ($t_{max}$).

20. Apparatus according to claim 18, characterized in that said heart rate determination means comprises electrocardiogram recording means and peak trigger means, said electrocardiogram recording means being set up for connection with electrocardiogram electrodes.

21. Apparatus according to claim 18, characterized in that said heart rate determination means comprises plethysmogram recording means and peak trigger means, said plethysmogram recording means being set up for connection with a plethysmogram transducer or an oxygen saturation transducer.

22. Apparatus according to claim 18, characterized in that said heart rate determination means comprises blood pressure recording means and peak trigger means.

* * * * *